United States Patent
Hennink et al.

(10) Patent No.: US 6,497,903 B1
(45) Date of Patent: Dec. 24, 2002

(54) HYDROLYSABLE HYDROGELS FOR CONTROLLED RELEASE

(76) Inventors: Wilhelmus Everhardus Hennink, Zuidplaslaan 120, 2743 CZ Waddinxveen (NL); Wendelmoed Nelletha Eleonora van Dijk-Wolthuis, van Swietenstraat 9, 2334 EA Leiden (NL)

( * ) Notice: Subject to any disclaimer, the term of this patent is extended or adjusted under 35 U.S.C. 154(b) by 0 days.

(21) Appl. No.: 09/214,306
(22) PCT Filed: Jul. 1, 1997
(86) PCT No.: PCT/NL97/00374
§ 371 (c)(1), (2), (4) Date: Jul. 20, 1999
(87) PCT Pub. No.: WO98/00170
PCT Pub. Date: Jan. 8, 1998

Related U.S. Application Data
(60) Provisional application No. 60/031,671, filed on Nov. 22, 1996.

(30) Foreign Application Priority Data
Jul. 1, 1996 (EP) .............................. 96201821

(51) Int. Cl.[7] ........................ A61K 9/10; A61K 47/36; A61K 47/32
(52) U.S. Cl. ................. 424/488; 424/487; 514/777; 514/772.6; 514/944; 516/105; 525/54.2
(58) Field of Search ............... 424/486, 487, 424/488; 514/777, 772.6, 944; 516/105; 525/54.2

(56) References Cited

U.S. PATENT DOCUMENTS 5,410,016 A  4/1995 Hubbell et al. ............. 528/354
5,567,435 A  10/1996 Hubbell et al. ............. 424/426

FOREIGN PATENT DOCUMENTS

EP  0 627 911  10/2000
WO  WO 93/09176  5/1993
WO  WO 93/19095  9/1993
WO  WO 94/01136  1/1994
WO  WO 94/02517  2/1994

OTHER PUBLICATIONS

De Smedt et al. "Characterization of the Network Structure of Dextran Glycidyl Methacrylate Hydrogels by Studying the Rheological and Swelling Behavior", Macromolecules 28, (1995) 5082–5088.
Den Otter et al., "Low Doses of Interleukin–2 Can Cure Large Bovine Ocular Squamous Cell Carcinoma", Anticancer Res. 13, (1993), 2453–2455.
Heller et al. "Controlled Release of Water–Soluble Macromolecules from Bioerodible Hydrogels", Biomaterials 4 (1983) 262–266.
Kim et al. "Hydrogels: Swelling, Drug Loading, and Release", Pharmaceutical Research 9(3) (1992) 283–290.
Rosenberg et al. "Treatment of 283 Consecutive Patients with Metastatic Melanoma or Renal Cell Cancer Using High–Dose Bolus Interleukin 2", JAMA 271, (1994) 907–913.
Soeterboek and Verheggen, "Biotechnologie Heeft de Toekomst" Pharm. Weekblad 130 (1995) 670–675.
Van Dijk–Wolthuis et al. "Synthesis, Characterization and Polymerization of Glycidyl Methacrylate Derivatized Dextran", Macromolecules 28, (1995) 6317–6322.
West et al., "Constant–Infusion Recombinant Interleukin–2 In Adoptive Immunotherapy of Advanced Cancer", New England Journal of Medicine 316, (1987), 898–905.
Hennink W.E. et al. (1996). *J of Controlled Release* 39(1):47–55.

Primary Examiner—Edward J. Webman
(74) Attorney, Agent, or Firm—Morrison & Foerster LLP (57) ABSTRACT

The present invention relates to a biodegradable hydrogel comprising bonds which are hydrolysable under physiological conditions. More particularly, the hydrogel consists of two interpenetrating polymer networks interconnected to one another through hydrolysable spacers. In addition, the invention relates to a method for the preparation of a hydrogel, wherein macromolecules, e.g., polymers which contain bonds which are hydrolysable under physiological conditions, are cross-linked in an aqueous solution.

19 Claims, 5 Drawing Sheets

Influence of spacer on the swelling ratio of dextran hydrogels

Figure 1. Influence of spacer on the swelling ratio of dextran hydrogels

Figure 2. Influence of the DS on the swelling ratio of dex-lactate-HEMA hydrogels Figure 3. Influence of the initial water content of dex-lactateHEMA hydrogels on the swelling ratio Figure 4. Swelling behaviour of dex-SA-HEMA hydrogels Figure 5. Release of IgG from degrading hydrogels (dex-lactate-HEMA, DS 2.5)

HYDROLYSABLE HYDROGELS FOR CONTROLLED RELEASE

This application was filed under 35 U.S.C. §111 claiming priority under 35 U.S.C. §120 from PCT/NL97/00374 filed Jul. 1, 1997 which designates the U.S. and which claims priority from European Application 96/201821.4 filed Jul. 1, 1996 and from U.S. Provisional Application No. 60/031,671 filed Nov. 22, 1996.

TECHNICAL FIELD

The present invention relates to hydrogels which have a good controlled release behaviour, and to processes to prepare such hydrogels.

BACKGROUND ART

The fast developments in the field of molecular biology and biotechnology have made it possible to produce a large number of pharmaceutically interesting products in large quantities. For instance, pharmaceutically active peptides and proteins can suitably be used as drugs in the treatment of life-threatening diseases, e.g. cancer, and of several types of viral, bacterial and parasital diseases; in the treatment of e.g. diabetes; in vaccines, e.g. for prophylactic aims, and for anticonception purposes. Especially the specialized biological activities of these types of drugs provide tremendous advantages over other types of pharmaceutics.

To illustrate the fast developments, it has been reported (see e.g. Soeterboek and Verheggen, Pharm. Weekblad 130 (1995) 670–675) that in the United States of America, about 275 biotechnological products are in phase IV studies, while more than 500 products are under investigation.

Examples of (recombinant) proteins, which are considered very interesting from a pharmacological point of view, are cytokines, such as interleukines, interferons, tumor necrosis factor (TNF), insulin, proteins for use in vaccines, and growth hormones.

Due to their nature, proteins and proteinaceous products, including peptides, which group of products will be referred to as protein drugs herein-below, cannot be administered orally. These products tend to degrade rapidly in the gastrointestinal tract, in particular because of the acidic environment and the presence of proteolytic enzymes therein.

Moreover, to a high extent protein drugs are not able to pass endothelial and epithelial barriers, due to their size and, generally, polar character.

For these reasons, protein drugs have to be brought in the system parenterally, i.e. by injection. The pharmacokinetical profile of these products is, however, such that injection of the product per se requires a frequent administration. For, it is a known fact that proteinaceous material is eliminated from the blood circulation within minutes.

In other words, since protein drugs are chemically and/or physically unstable and generally have a short half-time in the human or animal body, multiple daily injections or continuous infusions are required for the protein drug to have a desired therapeutic effect. It will be evident that this is inconvenient for patients requiring these protein drugs. Furthermore, this type of application often requires hospitabilization and has logistic drawbacks.

In addition, it appears that at least for certain classes of pharmaceutical proteins, such as cytokines which are presently used in e.g. cancer treatments, the therapeutic efficacy is strongly dependent on effective delivery, e.g. intra- or peritumoral. In such cases, the protein drugs should be directed to the sites where their activity is needed during a prolonged period of time.

Hence, there is a need for delivery systems which have the capacity for controlled release. In the art, delivery systems consisting of polymeric networks in which the proteins are loaded and from which they are gradually released have been proposed.

More in detail, at present, two major types of polymeric delivery systems can be distinguished: biodegradable polymers and non-biodegradable hydrogels.

Biodegradable polymers, e.g. polylactic acid (PLA) and copolymers of PLA with glycolic acid (PLGA), are frequently used as delivery systems for proteins.

Proteins can be incorporated in pharmaceutical delivery systems, e.g. microspheres, by a variety of processes. In vitro and in vivo, usually a biphasic release profile is observed: an initial burst followed by a more gradual release. The burst is caused by proteinaceous material present at or near the surface of the microspheres and by proteinaceous material present in pores. The gradual release is ascribed to a combination of diffusion of the proteinaceous material through the matrix and degradation of the matrix. Especially for larger proteins diffusion in these matrices is negligible, so that the release depends on the degradation of the polymer. The degradation can be influenced by the (co)polymer composition. A well-known strategy to increase the degradation rate of PLA is co-polymerization with glycolic acid.

Although delivery systems based on biodegradable polymers are interesting, it is very difficult to control the release of the incorporated protein. This hampers the applicability of these systems, especially for proteins with a narrow therapeutic window, such as cytokines and hormones. Furthermore, organic solvents have to be used for the encapsulation of the protein in these polymeric systems. Exposure of proteins to organic solvents generally leads to denaturation, which will affect the biological activity of the protein. Furthermore, the very stringent requirements of registration authorities with respect to possible traces of harmful substances may prohibit the use of such formulations of therapeutic drugs in human patients.

Also hydrogels are frequently used as delivery systems for proteins and peptides. Hydrogels can be obtained by crosslinking a water-soluble polymer yielding a three-dimensional network which can contain large amounts of water. Proteins can be loaded into the gel by adding the protein to the polymer before the crosslinking reaction is carried out or by soaking a preformed hydrogel in a protein solution. So, no (aggressive) organic solvents have to be used to load the hydrogels with protein molecules.

In contrast with the biodegradable polymers, the release of proteins from hydrogels can be easily controlled and manipulated by varying the hydrogel characteristics, such as the water content and the crosslink density of the gel. However, a major disadvantage of the currently used hydrogel delivery systems is that they are not biodegradable. This necessitates surgical removal of the gel from the patient after the release of the protein in order to prevent complications of inclusion of the empty hydrogel material (wound tissue is frequently formed).

Biodegradable hydrogels have been used in the preparation of delivery systems for protein drugs. One of these systems comprises crosslinked dextrans obtained by coupling glycidyl methacrylate (GMA) to dextran, followed by radical polymerization of an aqueous solution of GMA-derivatized dextran (dex-GMA). In this respect, reference is made to Van Dijk-Wolthuis et al. in Macromolecules 28, (1995), 6317–6322 and to De Smedt et al. in Macromolecules 28, (1995) 5082–5088.

Proteins can be encapsulated in the hydrogels by adding proteins to a solution of GMA-derivatized dextran prior to the crosslinking reaction. It appeared that the release of the proteins out of these hydrogels depends on and can be controlled by the degree of crosslinking and the water content of the gel (Hennink et al., J. Contr. Rel. 39, (1996), 47–57).

Although the described crosslinked dextran hydrogels were expected to be biodegradable, these hydrogels are rather stable under physiological conditions. This can is further elaborated in Example 5. It is shown among other that the dissolution time of dextran hydrogels obtained by polymerization of dextran derivatized with glycidyl methacrylate (DS=4) had a dissolution time of about 100 days. Dextran hydrogels, wherein the dextrans have a higher degree of substitution, did not show any signs of degradation during 70 days, even at extreme conditions.

DISCLOSURE OF THE INVENTION

The object of the present invention is to provide a slow or controlled release delivery system which does not possess the above-mentioned disadvantages, and especially does not require the use of organic solvents, does not show the undesired and uncontrollable burst effects, and do not possess a poorly controllable release behaviour. The present invention aims to combine the advantages of both types of known delivery systems, viz. a system, (bio)degradable under physiological conditions—either chemically and/or enzymatically—, with controlled protein drug release.

The present invention provides safe and easily controllable delivery systems, based on particular biodegradable hydrogels, which increase the applicability of protein drugs for the treatment of various diseases. The risks associated with these drugs, such as bursts in the release profile, and the inconvenience for the patient are reduced, while the therapeutic efficacy of drug treatments using the hydrogels of the present invention is increased.

More in detail, the present invention relates to a biodegradable hydrogel comprising bonds which are hydrolysable under physiological conditions. The hydrogels of the present invention contain hydrolytically labile spacers, which spacers are broken in human or animal bodies. As roughly indicated herein-above, a hydrogel is defined as a water-swollen, three-dimensional network of crosslinked hydrophilic macromolecules. More in detail, the hydrogels of the invention consist of two interpenetrating networks interconnected to one another through hydrolysable spacers. Hydrogels generally contain from 20 to more than 99 wt. % water.

Further, the invention relates to a method for the preparation of a hydrogen, wherein macromolecules, e.g. polymers, which contain bonds which are hydrolysable under physiological conditions, are crosslinked in an aqueous solution.

DETAILED DESCRIPTION OF INVENTION

In accordance with the present invention, all types of biodegradable hydrogels can be used, provided that hydrolytically labile spacers can be introduced in these structures. When brought into the system of an animal or human body, the hydrogel structure is more or less gradually broken down. The degradation products do not need to be removed after therapy; they can simply be metabolized and/or excreted by the body.

Preferably, the hydrogels are based on water soluble polymers which contain at least a number of side groups having the capability to form linkers to other polymers, e.g. dextran or derivatized dextrans, while starches and starch derivatives, cellulose derivatives such as hydroxyethyl and hydroxypropyl cellulose, polyvinylpyrrolidone, proteins, polyamino acids, polyvinylalcohol, polyacrylates, polymethacrylates, polyethylene glycols that contain a number of monomer units capable of forming side chains, and so on, can also be used, as well as copolymers thereof.

The hydrogels of the invention are suitably based on a polymer crosslinked with methacrylate units. Other crosslinking units are acrylate units, vinyl ethers and vinyl esters, as well as other units known for this purpose by the person skilled in the art.

Generally, the water-swellable polymers used in the present invention are made hydrolysable by introducing at least one hydrolytically labile unit in the spacers between the main chains of water soluble polymers and the second polymer chain formed by the crosslinkable units as described in the preceding paragraph. It is also possible to use polymer chains comprising hydrolytically labile monomer units in the main chain. However, not within the scope of the present invention are hydrogels which only contain polymer chains that are interconnected head-to-tail only by hydrolyzable spacer groups. Contrary to hydrogels according to the invention, in hydrogels based on swellable polymers which are only substituted with labile spacers head-to-tail, the degree of crosslinking is directly correlated to the water content of the gel. The polymer system the hydrogel of the invention, makes it possible to control the release of compound by adjusting the water content and/or the degree of crosslinking independently.

In a preferred embodiment, the hydrogels of the present invention comprise as hydrolytically labile units hydrolysable lactate and/or carbonate ester bonds. These bonds can be brought into the hydrogel by introducing e.g. (poly) glycolic acid and/or (poly)lactic acid residues between the main chain of the polymer and the crosslinkable groups of said polymer. With the term (poly)glycolic acid, glycolic acid as well as di- and oligomers thereof are meant. With the term (poly)lactic acid, lactic acid as well as di- and oligomers thereof are meant. Other possibilities for hydrolytically labile units are based on units introducing carboxylic esters, urethanes, anhydrides, (hemi)acetals, amides and peptide bonds.

In the most preferred embodiment of the present invention, (poly)glycolic acid and/or (poly)lactic acid spacers are introduced between polymerizable methacrylate groups and dextran. When a hydrogel formed of this material is introduced in a physiological environment, the hydrogel becomes biodegradable resulting in dextran, polyhydroxyethylmethacrylate (PHEMA), lactic acid and/or glycolic acid as degradation products. These degradation products are all biocompatible. It is noted that lactic acid and glycolic acid are endogenous compounds. Dextran is a non-toxic polymer, which is used for many years as plasma expander and is cleared by the kidneys depending on its molecular weight. PHEMA is a well-known biocompatible polymer, which is probably cleared via the kidneys, as well.

Hydrogels of the present invention can suitably be prepared by first synthesizing spacers which contain at least one crosslinkable group and at least one hydrolytically labile group; coupling such spacers to a water-soluble polymer, and crosslinking the polymers obtained, preferably in the presence of the compound to be released.

Preferred spacers within the present invention comprise a hydroxyethyl methacrylate (HEMA) group, coupled to one or more lactide and/or glycolide units, as exemplified in steps a and b of scheme 1. More in detail, HEMA-terminated polylactic acid pre-polymers can be synthesized by solution polymerization of lactide in toluene using HEMA as initiator and aluminium alkoxide as catalyst or by a bulk polymerization of lactide using HEMA as initiator and stannous octoate as catalyst. Dependent on the ratio HEMA/lactic acid pre-polymers which differ in molecular weight of the lactic acid block can be synthesized. HEMA terminated copolymers of glycolic acid and of glycolic acid-co-lactic acid can be synthesized in analogy. The pre-polymers can be characterized by known techniques, e.g. NMR and IR spectroscopy, differential scanning calorimetry (DSC), and gel permeation chromatography (GPC). In order to couple the HEMA terminated polylactic and/or glycolic acid pre-polymers to dextran, the terminal hydroxyl group has to be activated. Preferably, the binding of HEMA to dextran is effected by carbonyl-di-imidazole (CDI) as coupling agent. However, also other activation methods can be used. For example, reaction of the hydroxyl function of the HEMA lactic acid pre-polymer with succinic anhydride, followed by activation of the formed carboxylic group using established methods (e.g. dicyclohexylcarbodiimide (DCC) activation). The latter method yields dextran derivatives in which only hydrolytically instable ester bonds are present, which provide different degradation characteristics compared to the dextran derivatives synthesized with the CDI-method, in which both ester bonds and carbonate bonds are present.

The activated HEMA terminated polylactic and/or glycolic acid pre-polymers are subsequently coupled to dextran in a suitable aprotic so vent (such as DMSO), in the presence of a catalyst, e.g., N,N-dimethylaminopyridine (DMAP). The degree of substitution (i.e. number of moles of methacrylate groups containing prepolymer per 100 moles glucose units of dextran) can be tailored by the ratio of HEMA containing prepolymer versus dextran in the reaction mixture.

From these substituted polymers, hydrogels are prepared, e.g., by a radical polymerization of an aqueous solution of HEMA-pre-polymer functionalized dextran using a known initiator system of a tertiary amine and a persulphate (see e.g. the above cited articles of Van Dijk-Wolthuis et al. in Macromolecules 28, and Hennink et al. in J. Contr. Rel. 39). It is also possible to use polymerization by gamma irradiation, with the advantage that no initiator and/or catalyst residues have to be extracted from the hydrogel.

The hydrogel system of the present invention can easily be tailored with respect to protein drug release kinetics, which tremendously expand the applicability of protein drugs. Especially, in the case of biological response modifiers with a narrow therapeutic window, which are useful in the treatment of various diseases wherein the immune system is involved, this is very important.

An increasing degree of substitution (DS; amount of hydrolysable spacer containing crosslinkable branches per 100 main water-soluble polymer residues; determinable by $^1$H-NMR) yields a more crosslinked network. This results in a slower swelling rate and an increasing dissolution time of the gel.

The hydrogels of the present invention can be prepared in such a way that dissolution times from less than 1 day up to about 3 months and longer can be obtained. This can for instance be effected by varying the initial water content in the aqueous polymer solution to be crosslinked and the DS. Gels with a high initial water content, such as water contents higher than 85 wt. % predominantly contain intramolecular crosslinks, while lower initial water contents give more intermolecular crosslinking. Gels with less intermolecular crosslinks dissolve faster at the same DS.

Drugs can be loaded into hydrogels either by equilibration in a drug-containing solution (see e.g. Kim et al. in Pharm. Res. 9(3) (1992) 283–290) or by incorporation of the drug during the preparation of hydrogel (see e.g. Heller et al. in Biomaterials 4 (1983) 262–266).

Loading by equilibration, however, normally leads to a rather low drug content in the delivery system. This is especially the case, when the drug is a macromolecular compound. Unless the pore size of the hydrogel is rather large, the macromolecules will only adhere to the outer surface, which may lead to a burst release.

Therefore, preferably, the drug is loaded during polymerization or crosslinking.

Since microsphere suspensions are easy to prepare and are easily used for injection, the hydrogels generally will be applied as microspheres of varying sizes. Microspheres can be prepared by dissolving HEMA-derivatized dextran in water after which this solution is added to an oil phase (e.g. silicone oil) yielding a water-in-oil emulsion. After addition of a suitable initiator system, the methacrylate groups polymerize, yielding stable micropheres.

The drugs are released from the biodegradable hydrogels of the present invention during hydrolysis of the hydrogel, although at least to some extent diffusion of proteins from the hydrogel takes place. In fact, the hydrolysis behaviour of the hydrogel and the time during which compounds present in the hydrogel system are released can be adjusted to one another so that the release can take place at any level between first order (no degradation of the hydrogel) and zero order release (fully degradation controlled) (see in this respect Example 6, herein-below). This provides evident advantage over hydrogel systems that are not hydrolysable at physiological conditions, but which are rather stable, such as the known dextran-GMA hydrogel system, or over systems wherein the polymers in the hydrogel are elongated in one dimension only.

Protein drugs are released from the rather stable hydrogels following first order kinetics—protein release proportional to the square root of time—which is common for monolithic delivery systems. The hydrogels of the present invention, however, show a more zero order release behaviour—protein release proportional to time. When the hydrogel degrades during the release process, the diffusion coefficient of the protein drug, present in the hydrogel, increases. This leads to a more constant release in time.

The hydrogel system of the present invention offers—as said—the possibility to tailor the release profiles of encapsulated protein drugs. More in detail, the degradation rate of the hydrogel can be adjusted by varying the water content of the hydrogel, the degree of substitution, the number and length of hydrolysable groups in the spacers, and the choice of hydrolysable spacers.

It has been found that spacers based on glycolic acid have a higher hydrolytical sensitivity than spacers based on lactic acid. If glycolic acid based spacers are present an accelerated degradation rate of the hydrogel is observed as compared with lactic acid based spacers.

The effect of the water content of the hydrogel and the degree of substitution of the hydrogel polymers is elaborated in the examples following below.

Further, the rate of release depends on the size of the hydrogel particles. This size can be adjusted by varying the stirring speed, viscosity of the external phase etc. during the preparation of microspheres.

The rate of release does not depend on the length of the water soluble polymers, at least not to a high extent. This is contrary to hydrogel systems wherein the hydrolysable groups are present in the main chains of the polymer only (one dimensionally elongated polymers).

As indicated herein-above, the releasable compound can be a protein drug. However, it is also possible to encapsulate pharmacon containing nanoparticles, e.g. liposomes, iscoms, polylactic acid particles, polycaprolacton particles and gene delivery systems known to the person skilled in the art. The encapsulation of these nanoparticles has the advantage of preventing the occurence of a too fast release of the encapsulated compound, or, said in other words, burst-effects can be avoided in a more secure way.

An example of a loaded hydrogel system within the present invention is a hydrogel containing the cytokine interleukin-2 (IL-2). IL-2 is a protein drug which can e.g. be used in the treatment of particular types of cancer.

For IL-2 to be therapeutically effective in cancer treatment, prolonged presence of IL-2 at the site of tumor growth is required. This can be achieved either by administering high doses of IL-2 intravenously through frequent bolus injections (see e.g. Rosenberg et al. JAMA 271, (1994) 907–913), by prolonged continuous infusion (see e.g. West et al., N. Engl. J. Med. 316, (1987), 898–905, or by frequently administering low doses of IL-2 intra- or peri-tumorally (see e.g. Den Otter et al., Anticancer Res. 13, (1993), 2453–2455).

A major disadvantage of the intravenous route is that for obtaining sufficiently high levels of IL-2 at the site of tumor growth, such high doses of IL-2 have to be administered intravenously, that it becomes severely toxic. In contrast, the intra- or peri-tumoral approach, as developed by Den Otter et al., has proven to be very successful and virtually non-toxic in various transplanted and spontaneous tumors.

A serious problem for application of this form of therapy in human cancer patients, however, is that IL-2 has to be injected intra- or peri-tumorally 5 to 10 times within 1 to 2 weeks. For many types of cancer this is not-acceptable burden for the patient, like in cases of lung carcinoma, bladder cancer, and gastric cancer. In first attempts to translate the very effective local, low-dose IL-2 treatment to the human cancer clinic, these logistic problems of IL-2 delivery were already run into. The slow-release delivery system of the present invention makes the use of local IL-2 immunotherapies possible.

For the in vivo application hydrogel suspensions (microspheres) will normally contain up to $10^5$ I.U. of IL-2 in 0.5 ml, which are released over a period of 5 days (i.e. $2 \times 10^4$ I.U. of IL-2 released per day). The amount of protein released can be determined with sensitive quantitative detection methods (HPLC, ELISA assays). To investigate whether the released IL-2 is still biologically active and to what extent (i.e. what is the effect of these chemical procedures on the specific activity of IL-2), proliferation assays using the IL-2 dependent CTLL cell line can be performed.

The present invention will now be explained in more detail, while referring to the following, non-limiting examples.

EXAMPLES

To obtain a dextran hydrogel, first a polymerizable methacrylate group was introduced in dextran. For all reactions described below, dextran from Fluka (T40, $M_n$=15.000, $M_w$=32.500 g/mol) was used. Four different dextran derivatives were synthesized (Examples 1–4) in which the methacrylate ester was coupled via a spacer to dextran. The spacer contains different hydrolyzable bonds (carbonate and/or carboxylic ester). The degradation behaviour of gels prepared from these derivatives was compared with dextran gels derived from glycidylmethacrylate (dex-GMA). In this reference compound, the methacrylate ester is directly coupled to a hydroxyl group of dextran. This reference gel degrades extremely slowly.

Example 1

Synthesis of Dex-HEMA

Dextran derivatized with hydroxyethyl methacrylate (dex-HEMA) was synthesized by coupling carbonyldiimidazole (CDI) activated HEMA (HEMA-CI) to dextran.

CDI (1.62 g; 10 mmol) was dissolved in about 10 ml anhydrous tetrahydrofuran (THF). This solution was added to a solution of HEMA (1.30 g; 10 mmol) in 5 ml anhydrous THF. The reaction mixture was stirred for 16 hours at room temperature. After evaporation of the solvent a slightly yellow liquid was obtained (yield 2.93 g). The crude product was dissolved in ethylacetate, extracted with water to remove imidazole and unreacted HEMA and dried on anhydrous $MgSO_4$. After filtration, the solvent was evaporated and almost pure hydroxyethyl methacrylate activated with CDI (HEMA-CI) was obtained. The structure of this product was confirmed by NMR and IR spectroscopy.

Varying amounts of HEMA-CI (0.73, 1.49, or 2.19 g; 96% pure) were added to a solution of dextran (10 g, 62 mmole glucose units) and N,N-dimethylaminopyridine (DMAP; 2 g, 16.4 mmol) in anhydrous dimethylsulfoxide (DMSO; 90 ml). These reaction mixtures were stirred for 4 days at room temperature after which the reaction was terminated by the addition of about 2 ml of concentrated HCl. The reaction mixture was dialyzed against water for 3 days at 4° C. Dex-HEMA was isolated by lyophilization yielding a white fluffy material (yield>90%). The degree of HEMA substitution was determined by NMR spectroscopy, and amounted 4, 9, and 13, respectively.

Example 2

Synthesis of Dex-SA-HEMA

Dextran derivatized with the hemi-ester of succinic acid (SA) and HEMA (dex-SA-HEMA) was synthesized as follows.

SA (2.00 g, 20 mmol), HEMA (2,6 g, 20 mmol), triethylamine (TEA; 0.28 ml, 2 mmol) and hydrochinon (inhibitor,.

±10 mg) were dissolved in about 30 ml anhydrous THF. The reaction mixture was stirred for 2 days at 45° C., after which the solvent was evaporated. A yellow liquid was obtained (yield 4.88 g). The structure of HEMA-SA was confirmed by NMR and IR spectroscopy.

HEMA-SA (0.99 g (94% pure), 4 mmol) and dicyclohexylcarbodiimide (DCC; 0.83 g, 4 mmol) were dissolved in about 20 ml anhydrous DMSO. After 15 minutes a precipitate was formed (dicyclohexylureum; DCU) and this mixture was added to a solution of dextran (2.57 g, 16 mmol glucose units) and TEA (0.56.ml, 4 mmol) in anhydrous DMSO (20 ml). The resulting mixture was stirred for 3 days at room temperature, after which 3 drops of concentrated HCl were added to terminate the reaction. Next, the reaction mixture was filtered to remove DCU and dialyzed for 3 days at 4° C. After lyophilization, a white fluffy product was obtained (yield 2.78 g). The degree of substitution was established by NMR spectroscopy and amounted to 3.

Example 3

Synthesis of Dex-lactate-HEMA

Dextran derivatized with HEMA-oligolactide was synthesized as follows as illustrated in scheme 1. Three steps can be distinguished.
  a. coupling of lactate to HEMA yielding HEMA-lactate;
  b. activation of HEMA-lactate using CDI yielding HEMA-lactate-CI
  c. coupling of HEMA-lactate-CI to dextran.

A mixture of L-lactide (4.32 g; 30 mmol) and HEMA (3.90 g; 30 mmol) was heated to 110° C. Thereafter, a catalytic amount of stannous octoate (SnOct$_2$; 121.5 mg, 0.3 mmol) dissolved in about 0.5 ml toluene was added. The resulting mixture was stirred for 1 hour. After cooling down to room temperature, the mixture was dissolved in THF (20 ml). This solution was dropped in water (180 ml) and the formed precipitate was isolated by centrifugation. The pellet was taken up in ethyl acetate (40 ml), centrifugated to remove solid material, dried (MgSO$_4$) and filtered. The solvent was evaporated yielding a viscous oil (3.74 g, 45%). The product (HEMA-lactate) was characterized by NMR and IR spectroscopy.

HEMA-lactate (3.74 g, 10.8 mmol) was added to a solution of CDI (1.76 g, 10.8 mmol) in THF and stirred for 16 hours at room temperature. The solvent was evaporated under reduced pressure yielding a viscous oil. The product containing HEMA-lactate-CI and imidazole as major compounds (NMR analysis) was used without further purification.

To a solution of dextran (10 g, 62 mmol glucose units) and DMAP (2.0 g, 10.6 mmol) a varying amount of HEMA-lactate-CI was added (1.61, 3.23 or 4.84 g respectively, 80% pure). These mixtures were stirred for 4 days at room temperature after which the reaction was terminated by the addition of about 2 ml of concentrated HCl. The solutions were dialyzed against water for 2 days. After lyophilization, white fluffy products were obtained (yield around 85%). The degree of substitution (as determined by NMR spectroscopy) amounted to 3, 6 and 10 for the three products, respectively.

Using similar procedures, the length of the lactate spacer can be varied by changing the molar ratio of HEMA and lactide in the first reaction.

Example 4

Synthesis of Dex-glycolide-HEMA

Dex-glycolide-HEMA was synthesized according to the same procedure as described in Example 3 replacing lactate by glycolide.

Reference Example 1

Dex-GMA

Dex-GMA was synthesized as described by Van Dijk-Wolthuis et al., Macromolecules 28, (1995), 6317–6322. An reinvestigation of the obtained dextran derivative revealed that the methacrylic ester group is directly coupled to one of the hydroxylic group of dextran, meaning that the glyceryl spacer is not present.

Example 5

Preparation of Dextran Hydrogels

Hydrogels were obtained by a free radical polymerization of aqueous solutions of methacrylated dextran (prepared according to Examples 1–4 and Ref. Example 1). Methacrylated dextran (100 mg) was dissolved in 760 µl PBS buffer (10 mM phosphate, 0.9% NaCl, 0.02% NaN$_3$, pH 7.2). To this solution 90 µl of potassium peroxydisulfate (KPS; 50 mg/ml) in the same buffer was added per gram solution and mixed well. Subsequently, N,N,N'N'-tetramethylethylenediamine (TEMED; 50 µl; 20% (v/v) in water, pH adjusted to 7) was added and the resulting solution was quickly transferred into an Eppendorf tube and polymerized for 1 hour at room temperature yielding a hydrogel material with an initial water content of about 90% (w/w) after polymerization.

The gels were removed from the tubes, accurately weighed and incubated in PBS at 37° C. Periodically, the weight of the gels was determined and used to calculate the degree of swelling (=$W_t/W_o$, in which $W_t$ is the weight of the gel at time t and $W_o$ is the initial weight of the gel). The hydrogel degradation (dissolution) time is defined as the time at which the swelling ratio=0 (or $W_t$=0).

Figure 1:
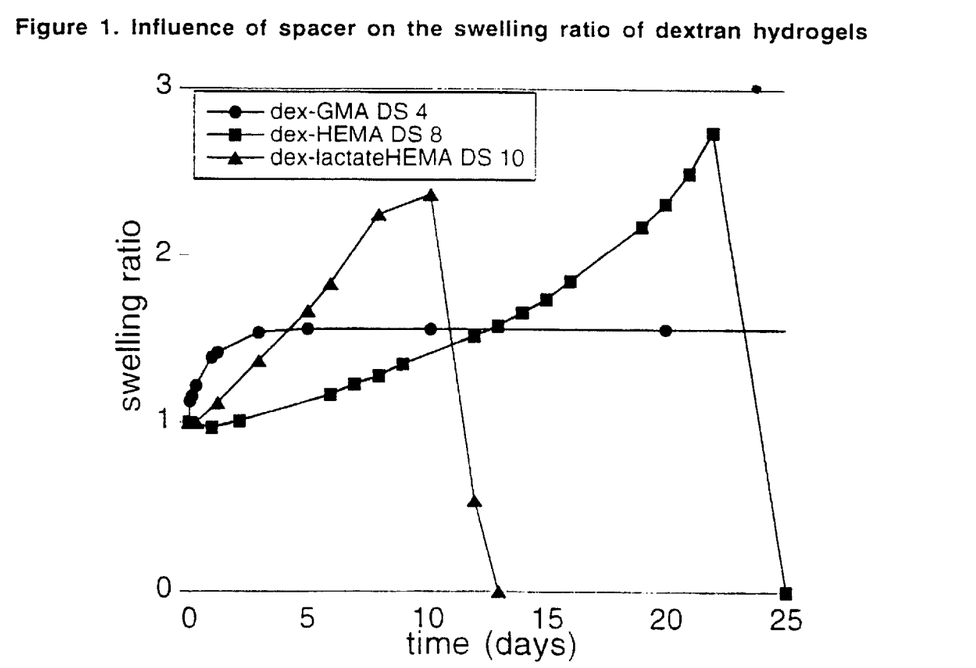
FIG. 1 illustrates the influence of the spacer on the swelling ratio of dextran hydrogels.

FIG. 1 shows the swelling behaviour of three different dextran hydrogels (initial water content 90%). The dex-GMA (DS=4) reached an equilibrium swelling within 3 days; thereafter the weight of the gels remained constant indicating that no significant hydrolysis of methacrylate esters occurred. Dex-HEMA and dex-lactate-HEMA showed a progressive swelling in time until these gels dissolved completely. This demonstrates that in these hydrogel systems hydrolysis of carbonate esters (dex-(lactate) HEMA) and/or lactate esters (dex-lactateHEMA) occurred.

Figure 2:
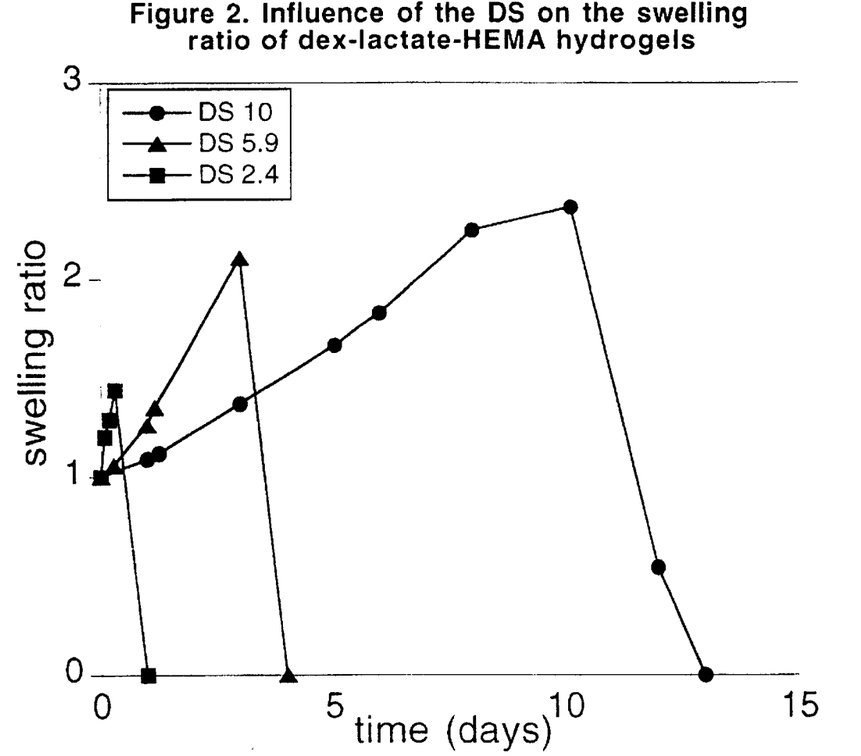
FIG. 2 illustrates the influence of the DS on the swelling ratio of dex-lactate-HEMA hydrogels.

FIG. 2 shows the swelling behaviour of dex-lactateHEMA hydrogels (initial water content 92%) and varying degree of substitution. As can be seen an increasing DS resulted in an increasing dissolution time.

Figure 3:
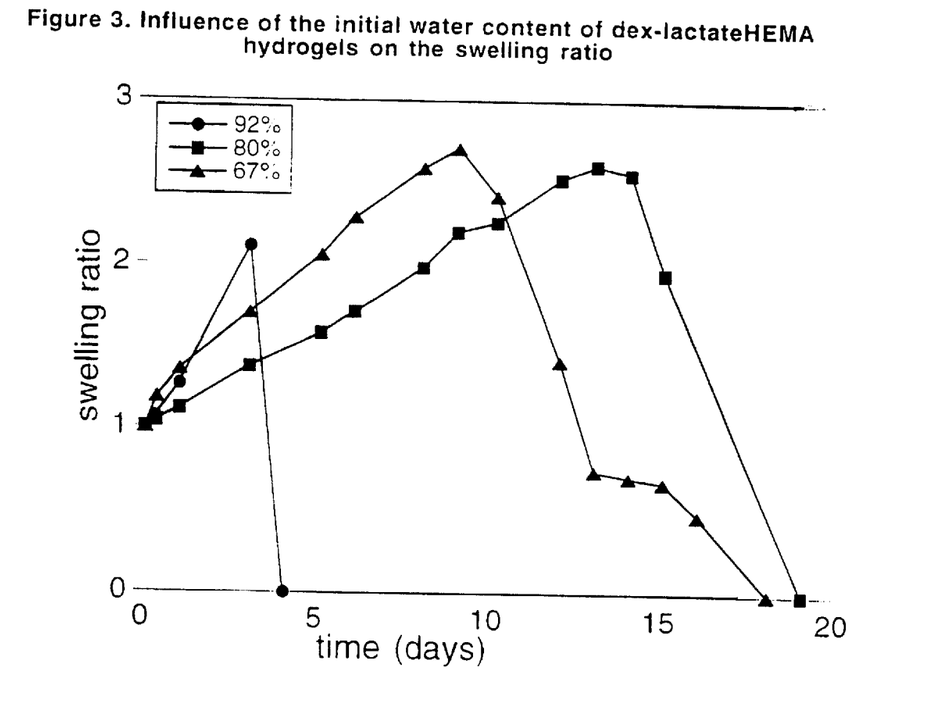
FIG. 3 illustrates the influence of the initial water content of dex-lactate HEMA hydrogels on the swelling ratio.

FIG. 3 shows the swelling behaviour of dex-lactateHEMA hydrogels with a fixed DS (6) and varying initial water content. It appears that the dissolution time increases with an increasing initial water content.

Figure 4:
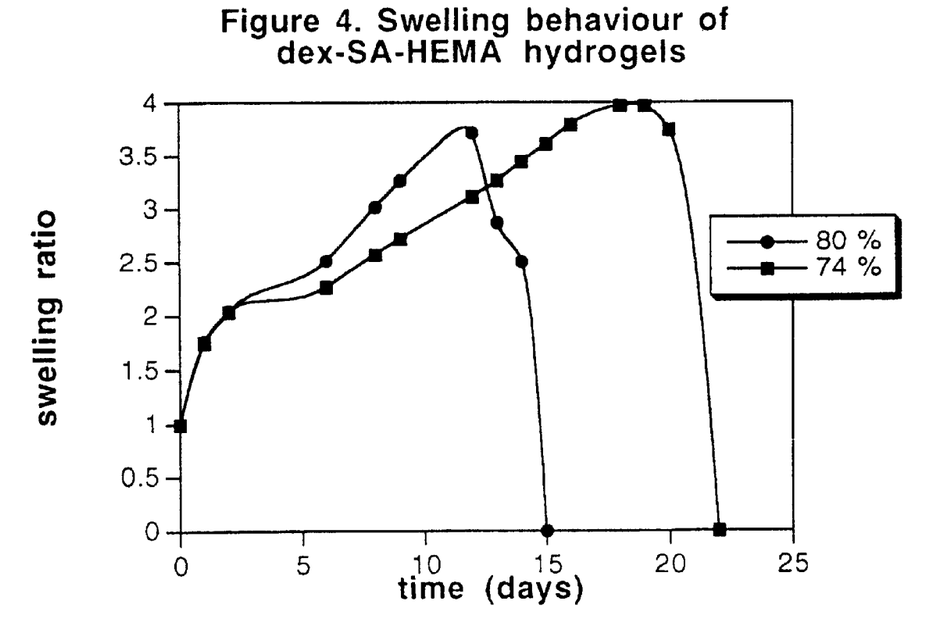
FIG. 4 illustrates the swelling behavior of dex-SA-HEMA hydrogels.

FIG. 4 shows the swelling behaviour of dex-SAHEMA hydrogel (DS 3) and a varying initial water content.

The next tables give an overview of the dissolution times of different dextran hydrogels.

| dissolution time (days) of dex-lactate-HEMA gels | | | |
| --- | --- | --- | --- |
| initial water content | DS 10 | DS 6 | DS 2.5 |
| 90% | 8–13 | 4 | 1–2 |
| 80% | 16 | 7–18 | 3–9 |
| 70% | 22 | 10–19 | 6–10 |

-continued

| dissolution time (days) of dex-HEMA gels | | | |
|---|---|---|---|
| initial water content | DS 8 | DS 17 | DS 20 |
| 92% | 25 | 42 | 55 |
| 80% | 53 | 100 | ND |
| 67% | 70 | >100 | ND |

| dissolution time (days) of dex-HEMA-SA gels | |
|---|---|
| initial water content | DS 3 |
| 80% | 15 |
| 74% | 23–28 |
| 60% | 44 |

The dissolution time of dextran hydrogels (initial water content 92%) obtained by polymerization of dextran derivatized with GMA (DS 4) had a dissolution time of about 100 days (pH 7.2, 37° C.). Gels obtained by polymerization of dextran derivatized with GMA (initial water content 80%, DS 11) did not show any signs of degradation (increased swelling) during 70 days, even at extreme conditions (37° C., pH 12 and pH 1).

Example 6

Protein Release From Degrading Dextran Hydrogels

The release from non-degrading dex-GMA hydrogels has been studied extensively. It appeared that when the protein diameter was smaller than the hydrogel mesh size, the release of the protein could be effectively described by the free volume theory. In this case the cumulative amount of protein released was proportional to the square root of time (W. E. Hennink, Controlled release of proteins from dextran hydrogels, Journal of Controlled Release 39, (1996), 47–55).

Figure 5:
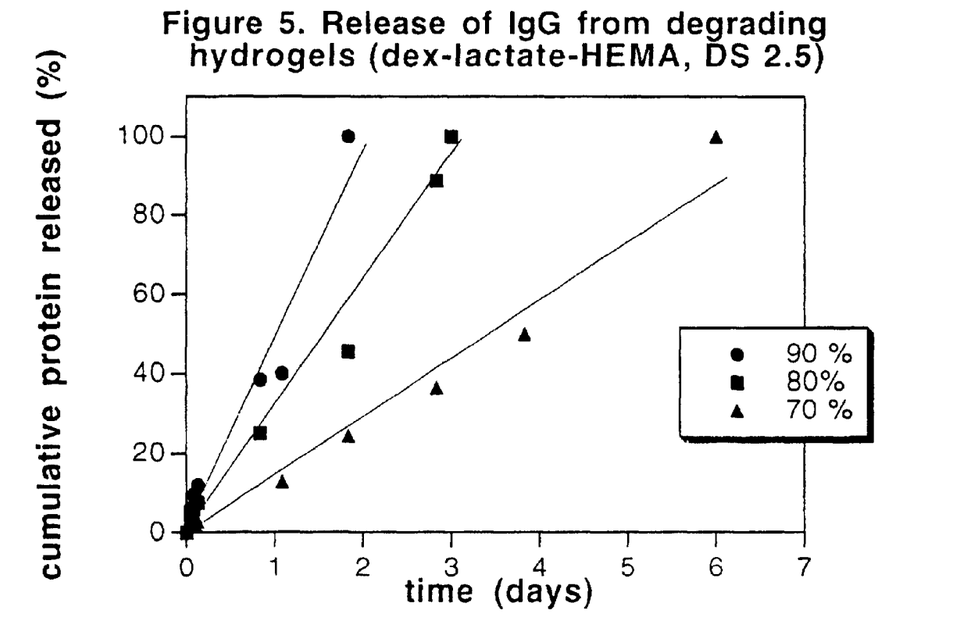
FIG. 5 illustrates the release of 1 gG from degrading hydrogels (dex-lactate-HEMA, DS 2.5)

FIG. 5 shows the release of a model protein (IgG) from degrading dextran hydrogels (dex-lactate-HEMA, DS 2.5). The release of IgG from these degrading gels is zero order (cumulative release proportional to time). This is in contrast with the release of proteins from non-degrading dextran hydrogels, where a first order release has been observed.

What is claimed is:

1. A biodegradable hydrogel comprising a network of polymer chains,
   wherein said polymer chains are interconnected to one another through spacers,
   wherein the spacers comprise a crosslinking unit and one or more bonds which are hydrolysable under physiological conditions,
   wherein the crosslinking unit is derived from a hydroxyalkyl methacrylate unit, and
   wherein the bonds which are hydrolysable are selected from the group consisting of carbonate bonds, carboxylic acid ester bonds, urethane bonds, anhydride bonds, (hemi)acetal bonds, amide bonds, and mixtures of said bonds, and
   wherein the polymer chains are based on dextran or derivatised dextran, and wherein said ester bonds are optionally those of lactate, glycolate, or succinate.

2. The hydrogel of claim 1, wherein the crosslinking unit is derived from a hydroxyethyl methacrylate.

3. The hydrogel of claim 1, wherein the bonds are selected from the group consisting of bonds contained in lactate units, bonds contained in glycolate units and bonds contained in mixtures of lactate and glycolate units.

4. The hydrogel of claim 1, further comprising a drug.

5. The hydrogel of claim 3, further comprising a drug.

6. The hydrogel claim 4, wherein the drug is a proteinaceous material.

7. The hydrogel of claim 5, wherein the drug is a proteinaceous material.

8. A crosslinkable polymer capable of forming a hydrogel,
   comprising a hydrophilic polymeric backbone based on dextran or derivatised dextran and at least one spacer,
   the spacer comprising a bond which is hydrolysable under physiological conditions and at least one hydroxyalkyl methacrylate group,
   wherein the bond which is hydrolysable is selected from the group consisting of carbonate bonds, carboxylic acid ester bonds, urethane bonds, anhydride bonds, (hemi)acetal bonds, amide bonds, and mixtures of said bonds, and
   wherein said ester bonds are optionally those of lactate, glycolate, or succinate.

9. The crosslinkable polymer of claim 7, wherein the spacer comprises at least one hydroxyethyl methacrylate group.

10. The crosslinkable polymer of claim 7, wherein the spacer comprises one carbonate ester bond.

11. The crosslinkable polymer of claim 7, wherein the spacer comprises bonds contained in lactate units, bonds contained in glycolate units, or bonds contained in mixtures of lactate and glycolate units.

12. A crosslinked polymer capable of forming a hydrogel, obtained by crosslinking the crosslinkable polymer of claim 8.

13. A crosslinked polymer capable of forming a hydrogel, obtained by crosslinking the crosslinkable polymer of claim 10.

14. A crosslinked polymer capable of forming a hydrogel, obtained by crosslinking the crosslinkable polymer of claim 11.

15. A method for preparing a hydrogel comprising a network of polymer chains,
   which method comprises crosslinkable polymer of claim 8 in an aqueous medium.

16. The method of claim 15, comprising crosslinking the crosslinkable polymer of claim 10.

17. The method of claim 15, comprising crosslinking the crosslinkable polymer of claim 11.

18. The method of claim 15, wherein a drug is present during the crosslinking step.

19. The method of claim 18, wherein the drug is a proteinaceous material.

* * * * *